(12) United States Patent
Kuefner

(10) Patent No.: US 10,980,830 B2
(45) Date of Patent: Apr. 20, 2021

(54) SYSTEMS AND METHODS FOR TREATING SKIN CONDITIONS WITH MAGNESIUM ION COMPOSITIONS

(71) Applicant: George C. Kuefner, Arlington Heights, IL (US)

(72) Inventor: George C. Kuefner, Arlington Heights, IL (US)

( * ) Notice: Subject to any disclaimer, the term of this patent is extended or adjusted under 35 U.S.C. 154(b) by 173 days.

(21) Appl. No.: 15/969,340

(22) Filed: May 2, 2018

(65) Prior Publication Data
US 2018/0318341 A1 Nov. 8, 2018

Related U.S. Application Data

(60) Provisional application No. 62/500,720, filed on May 3, 2017.

(51) Int. Cl.
*A61K 33/06* (2006.01)
*A61K 9/00* (2006.01)
(Continued)

(52) U.S. Cl.
CPC ............ *A61K 33/06* (2013.01); *A61K 9/0009* (2013.01); *A61K 9/0021* (2013.01); *A61K 9/7007* (2013.01); *A61K 9/7023* (2013.01); *A61L 15/28* (2013.01); *A61L 15/44* (2013.01); *A61L 15/58* (2013.01); *A61N 1/0448* (2013.01); *A61N 1/30* (2013.01); *A61P 17/06* (2018.01)

(58) Field of Classification Search
CPC .... A61K 33/06; A61K 9/7007; A61K 9/7023; A61K 9/0009; A61K 9/0021; A61L 15/44; A61L 15/28; A61L 15/58; A61N 1/30; A61N 1/0448; A61P 17/06
See application file for complete search history.

(56) References Cited

U.S. PATENT DOCUMENTS 5,898,037 A * 4/1999 Marx .................... A61Q 19/08
424/49
5,962,477 A  10/1999 Mak
(Continued)

FOREIGN PATENT DOCUMENTS

WO  2006112690  10/2006

OTHER PUBLICATIONS

International Search Report of the International Searching Authority prepared by the USPTO in connection with PCT/US2018/030705, dated Jul. 13, 2018; Entire Document (2 pages).
(Continued)

*Primary Examiner* — Amber R Stiles
(74) *Attorney, Agent, or Firm* — K&L Gates LLP

(57) ABSTRACT

The present disclosure provides for systems and methods including pre-moistened dressings with a treatment composition, wherein the dressings can include a water proof occlusive material on one side and an absorbing material for the treatment composition, thereby enabling direct contact transfer of the treatment composition to the skin surface. The treatment composition can include 2-70% wt/vol of a magnesium complex in water. The dressings can be replaced every one to three days for a total treatment time of one to 36 days or more. The treatment systems can be used to treat psoriasis and chronic inflammation, among others.

8 Claims, 4 Drawing Sheets

(51) Int. Cl.
     *A61L 15/44*         (2006.01)
     *A61N 1/30*          (2006.01)
     *A61L 15/28*         (2006.01)
     *A61P 17/06*         (2006.01)
     *A61N 1/04*          (2006.01)
     *A61L 15/58*         (2006.01)
     *A61K 9/70*          (2006.01)

(56) References Cited

U.S. PATENT DOCUMENTS

| | | | |
|---|---|---|---|
| 6,010,715 A * | 1/2000 | Wick | A61K 9/7084 |
| | | | 424/448 |
| 8,486,426 B2 | 7/2013 | Maley et al. | |
| 2007/0292492 A1 | 12/2007 | Friden | |
| 2010/0119584 A1* | 5/2010 | Matsuzawa | A61K 9/7053 |
| | | | 424/447 |
| 2011/0217358 A1 | 9/2011 | Feleki et al. | |
| 2014/0276475 A1 | 9/2014 | Taylor | |

OTHER PUBLICATIONS

Written Opinion of the International Searching Authority prepared by the USPTO in connection with PCT/US2018/030705, dated Jul. 13, 2018; Entire Document (6 pages).

* cited by examiner

SYSTEMS AND METHODS FOR TREATING SKIN CONDITIONS WITH MAGNESIUM ION COMPOSITIONS

CROSS-REFERENCE TO RELATED APPLICATIONS

This application incorporates by reference and claims the benefit of priority to U.S. Provisional Application 62/500,720 filed on May 3, 2017.

BACKGROUND OF THE INVENTION

The present subject matter relates generally to treatment, mitigation, prevention, and cosmetic improvement of plaque psoriasis and the treatment of adhesive capsulitis and chronic pain with transdermal delivery of magnesium ions.

Plaque psoriasis affects 1-3% of the population. Psoriasis is characterized by reddened inflamed papules that coalesce to form round or oval, silvery, scaling plaques distinguished from normal surrounding skin. The exact cause of psoriasis is unknown, however, genetic predisposition, skin injury, emotional stress, infections, environmental factors and certain drugs have been implicated. The disease is characterized by chronic lifelong exacerbations and remissions causing physical and emotional distress.

One focus of psoriasis treatment has been the use of systemic TNF-alpha inhibitors (Skin Therapy Letter. 2004; 9(10)) for patients with moderate to severe plaque psoriasis. Drawbacks to systemic treatments have been serious adverse side effects and cost of multiple thousands of dollars a year. Current treatments for patients with mild plaque psoriasis remain topical steroids, coal tar preparations, and topical moisturizers. While these treatments usually result in improvement of the psoriasis, it is not usual for longer term remission to occur. Coal tar preparations are messy to apply while topical steroids can be associated with atrophy of the skin. Moisturizers generally improve the appearance of plaque psoriasis by improving scaliness, however, complete remissions are not typical.

Accordingly, there is a need for a simple, cost-effective, and efficacious system and method for treating patients with plaque psoriasis.

Further, chronic inflammatory conditions involving the joints and spine are the cause of immeasurable morbidity and loss of productivity. Current treatments rely on systemic non steroidal anti-inflammatory agents (NSAIDs) taken orally, orally administered corticosteroids and injections of corticosteroids usually in combination with a local anesthetic into the affected joint or spine.

Accordingly, there is also a need for a simple and cost effective treatment for patients who cannot tolerate NSAIDs or who cannot take them do to other concomitant medical conditions such as gastrointestinal disease. There is also a need for a simple and cost effective treatment for patients who want to avoid the side effects related to the long term use of oral corticosteroids or those who cannot take corticosteroids do to concomitant medical conditions. Further there is a need for effective relief of pain for chronic inflammatory conditions of the joints and spine without addictive potential.

BRIEF SUMMARY OF THE INVENTION

Transdermal administration of magnesium ions has been shown to be effective in causing benefit in three chronic inflammatory conditions discussed in this application, plaque psoriasis, adhesive capsulitis (frozen shoulder), and chronic low back syndrome. These and numerous other chronic inflammatory conditions have been shown to be associated with elevated TNF alpha levels. Elevated TNF alpha may be considered a biomarker in determining which other chronic inflammatory and chronic pain conditions are likely to benefit from the administration of transdermal magnesium therapy.

Transdermal magnesium ions appear to be an ideal candidate for treating chronic inflammatory conditions affecting joints and spine in that they induce local anesthesia, have been associated with decreasing TNF alfa levels in pre-eclamptic placentas, clinically were found to have anti-inflammatory effects in the three conditions sited in this application, have been shown to have vasodilatory effects on the vasculature (See, Mechanisms responsible for vasodilation upon magnesium infusion in vivo: clinical evidence, Magnesium Research, 2002 December; 15 (3-4):241-6, incorporated herein by reference) evidenced by transient localized hyperemia upon removal of the embodiments.

Intra-dermal injections of 1% magnesium sulfate is effective in improving a small area of recurrent plaque psoriasis. Intra-dermal treatment would appear to be impractical with the associated pain and discomfort associated with the injections which would be compounded in the treatment of plaque psoriasis affecting larger surface areas. In addition, the clearance rate of the magnesium solution from the extracellular fluid would inherently seem to be measurable in minutes rather than hours. It would be reasonable to assume that transdermal delivery of lower concentrations of magnesium ions over longer periods of time would allow for greater intracellular transport of the magnesium ions to affect a therapeutic response.

Any conventional transdermal drug delivery system should be sufficient and modifiable to administer magnesium ions through the skin in sufficient quantity to effect benefit in plaque psoriasis, adhesive capsulitis and chronic lower back pain (e.g., chronic low back syndrome). Conventional transdermal drug delivery systems can include a classic reservoir patch, a polymer reservoir patch, a matrix patch (drug in adhesive patch), a multi-laminate solid-state reservoir patch, a matrix diffusion patch, a micro-reservoir patch, and conventional self-contained iontophoresis devices.

The components of the transdermal delivery system can include any suitable commercially available components, or components modified in manor suitable to deliver magnesium ions in sufficient quantity to benefit plaque psoriasis, adhesive capsulitis and chronic low back pain and other chronic inflammatory conditions.

The present disclosure provides for systems and methods for treating psoriasis and chronic inflammation including pre-moistened medical dressings (e.g., medical pads, bandages) and/or ionphoresis pads with a treatment composition, wherein the dressings can include a water proof occlusive material on one side and a material suitable for absorbing or holding the treatment composition on the other side, thereby enabling direct contact transfer of the treatment composition to the skin surface. The treatment composition can include 2-70% wt/vol of magnesium chloride and/or magnesium sulfate in water. The dressings can be worn from one to 24-48 hours, and replaced every one to three days for a total treatment time of one to 36 days, or longer.

Conventional treatments for plaque psoriasis or psoriasis have been focused on improving barrier function of the skin with a multifaceted approach as reflected in the lists of necessary ingredients. In addition, the conventional methods fail to require for use of occlusive material over the composition.

In an example, the treatment system for a psoriasis outbreak, the treatment system comprising: a composition including 20-70% wt/vol of a magnesium complex in water; a medical dressing, wherein 1-6 mL the composition is applied one side of the medical dressing.

In an example, the disclosure provides a treatment method for psoriasis, the method comprising: providing a plurality of treatment patches, wherein each treatment patch includes a composition including 20-70% wt/vol of a magnesium complex in water, and a medical dressing, wherein one side of the medical dressing includes 1-6 mL of the composition; applying a treatment patch to a psoriasis outbreak for 1 to 24 hours; and replacing the applied treatment patch with a new treatment patch every 24-48 hours for 10-40 days.

In an example, the disclosure provides a treatment method for an inflammatory disorder, the method comprising: providing a medical dressing impregnated 1-5 mL of 20-60% wt/vol of a magnesium complex; applying the medical dressing to a treatment location; and replacing the medical dressing after 8-48 hours.

An advantage of the present systems and methods is that the composition need only include one ingredient in a solvent, rendering a simple, yet efficacious and cost effective treatment.

A further advantage of the present system is providing a treatment composition already applied to a dressing, such that a patient merely applies the dressing to the treatment area. Therefore, patients do not need to measure a specific dose or apply the dose and dressing separately.

Another advantage of the present system is providing another option for physicians in the treatment of plaque psoriasis that can easily be applied in a doctor's office while allowing interaction with health care professionals instructing the patient on the application, removal and replacement while in the office. The healthcare professionals do not have to measure a specific dose or apply the dose separately.

A further advantage of different sizes and shapes of the system would allow the health care professional to choose an appropriate size, shape and dosage determined by the body part the system was to be applied to.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Magnesium ions have been used in the management of pre-eclampsia in the form of magnesium sulfate. The possible therapeutic effect of magnesium sulphate in the disease process of pre-eclampsia has been found to be the down regulation of placental TNF-alpha secretion. (Possible therapeutic effect of magnesium sulfate by the down regulation of placental tumor necrosis factor-alpha, European Cytokine Network Volume 21, issue 1, March 2010; Magnesium Decreases Inflammatory Cytokine Production: A Novel Innate Immunomodulatory Mechanism, Journal Immunology, May 18, 2012, both incorporated herein by reference)

Further, it has been observed that TNF alpha levels are decreased as the psoriasis severity decreases. Specifically, serum TNF-alpha levels correlate with disease severity and are reduced by effective therapy in plaque-type psoriasis. (J. Biol. Homeost. Agents, 1997 July-September; 11(3): 115-8) One hypothesis is that epidermal hyperplasia and inflammation release cytokines that set in motion a vicious cycle releasing the secretion of more cytokines. TNF alpha is one of the key mediators of epidermal keratinocyte hyperplasia. (Cracking the cytokine code in psoriasis, Nature Medicine 13, 242-244 2007; The immunological basis for the treatment of psoriasis with new biological agents. J Am. Acad. Dermatology 46(1):1-23, January 2002).

The uncontrolled feedback mechanism causing increased secretion of TNF-alpha in pre-eclampsia placentas may be similar to the uncontrolled pro-inflammatory feedback mechanism and localized to increase production of TNF-alpha in plaque psoriasis and other chronic inflammatory conditions. The present systems and methods can interrupt the "viscous cycle" feedback mechanism in plaque psoriasis by topically applied magnesium cations via passive diffusion.

The present system and methods include absorption of magnesium cations into the body via transdermal delivery that is effective in breaking the pro-inflammatory "vicious cycle" feedback mechanism of psoriasis. The present treatment composition can include a solution of a magnesium complex (e.g, magnesium chloride, magnesium sulfate, among others) in water at a concentration between, and including, 2-70% wt/vol, 20-50% wt/vol, 20-60% wt/vol, 45-70% wt/vol, 55-65% wt/vol, 5-70 wt/vol, and/or 55-60% wt/vol. In an example, warm tap water is added to 140 grams of magnesium chloride flakes (Life-Flo 100% Pure Magnesium Flakes with trace elements) to make 8 ounces of solution 58% wt/vol.

Figure 1:
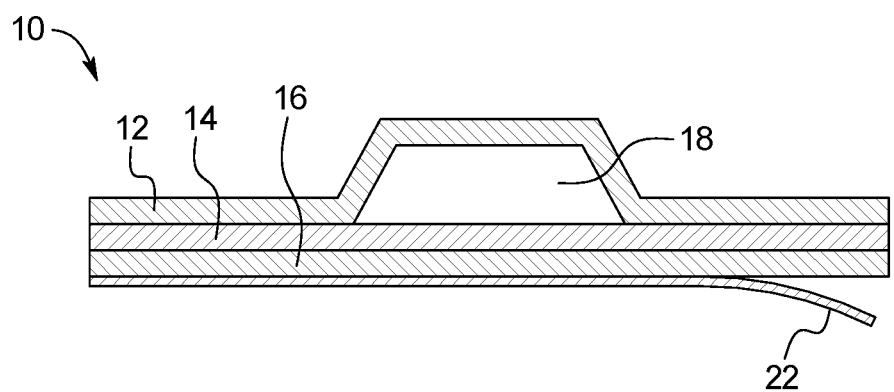
FIG. 1 is a schematic of an example of a delivery system including a drug reservoir.

In an example, the treatment system can include a drug reservoir delivery system, as shown in FIG. 1. For example, the system 10 can include an outer impermeable backing layer 12 encasing the drug reservoir 18, a middle polymer rate control membrane 14, and a bottom adhesive layer that can include a release liner 22 to be removed before application to the skin.

The present disclosure provides for systems and methods including pre-moistened (not saturated) dressings (e.g., medical pads, bandages, etc.) manufactured with a water proof occlusive material on one side and a material suitable for absorbing or holding the solution on the other side and allowing direct contact transfer of the solution to the skin surface. For example, the pad can include porous material or absorbent material suitable for holding the present composition. The pad can include a gelatinous film or layer and/or an adhesive film or layer suitable for holding and releasing the present composition to the skin while also acting as an adhesive to hold the pad against the skin such as an occlusive hydrocolloid or nearly occlusive hydrocolloid membrane. The gelatinous film or layer, or any suitable adhesive film or layer could also serve in a rate limiting manner to control the flux of magnesium ions through the skin. The dressings can have an adhesive border surrounding the pad wide enough to hold the pre-moistened material in direct contact with the skin to be treated. Alternatively, the dressings can have no adhesive border and be kept in place with and wrapping material suitable to hold the pre-moistened pad in place such as Medi-Rip self adherent bandages, distributed by Hartmann USA Inc. The dressings can also be kept in place with any compressive sleeve or leggings.

Figure 2:
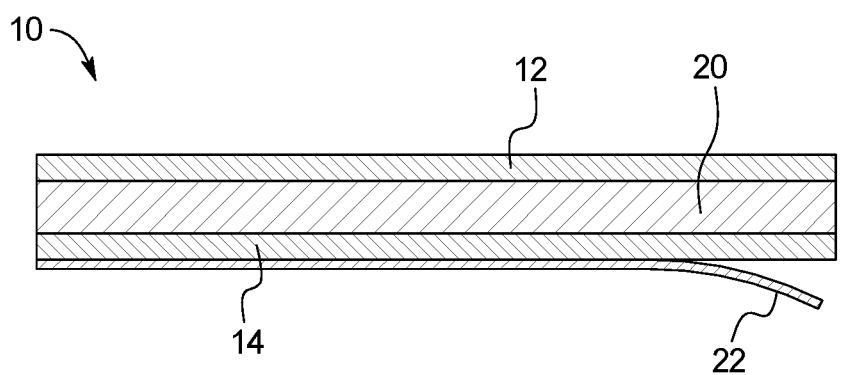
FIG. 2 is a schematic of an example of a delivery system including a polymeric reservoir.
Figure 3:
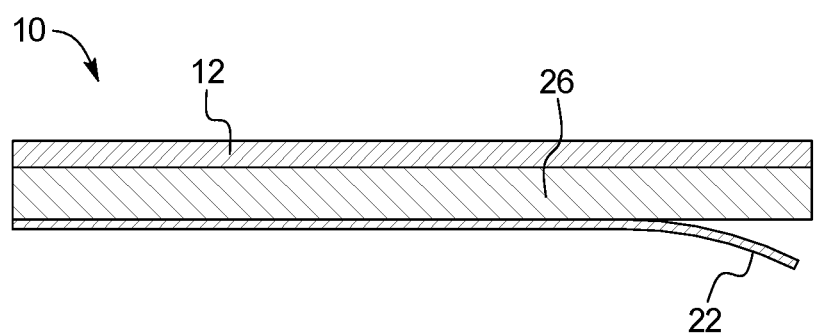
FIG. 3 is a schematic of an example of a delivery system including a matrix.

The treatment system can include a plurality of layers, wherein the layers can be configured in a number of manners. For example, as shown in FIG. 2, the treatment system 10 can include an impermeable backing layer 12, a polymer 20 dispersed with the magnesium composition, a rate controlling adhesive polymer 14, and a release liner 22. Alternatively, or in addition to, the treatment system 10 can include a drug adhesive matrix encased between the backing layer 12 and the releasable liner 22, as shown in FIG. 3.

Figure 4:
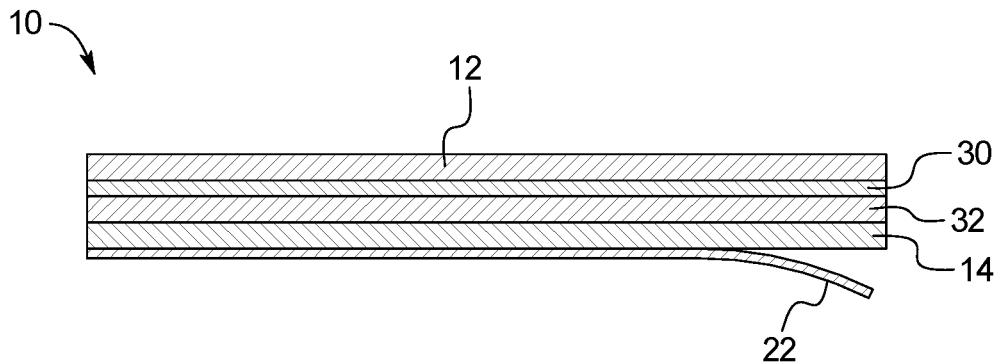
FIG. 4 is a schematic of an example of a delivery system including an adhesive dispersion.

In yet another example, as shown in FIG. 4, the treatment system 10 can include the impermeable backing 12, an adhesive layer 30, a drug reservoir layer 32, a rate controlling adhesive layer 14, and a release liner 22.

Figure 5:
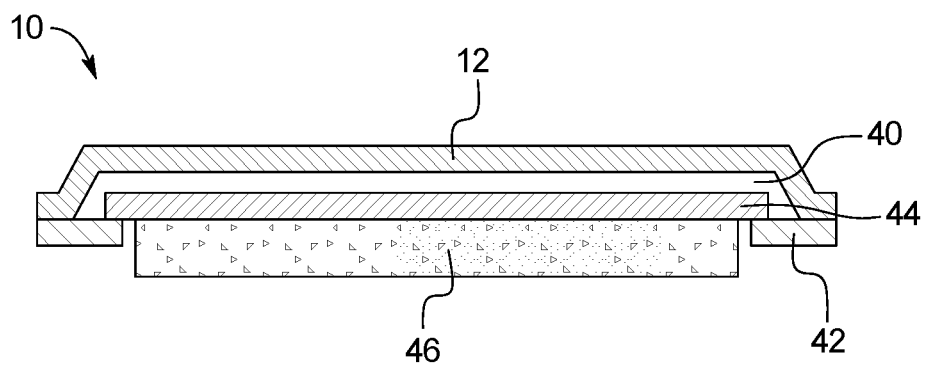
FIG. 5 is a schematic of an example of a delivery system including a matrix diffusion including a hydrophilic polymer matrix.

As shown in FIG. 5, the treatment system 10 can include a matrix diffusion system. For example, the treatment system 10 can include an outer impermeable backing 12, an absorbent backing pad 40, an occlusive backing plate 44, a hydrophilic polymeric matrix reservoir 46 to be in direct contact with a user's skin, and an outer adhesive rim 42 surrounding the hydrophilic polymeric matrix reservoir 46.

Figure 6:
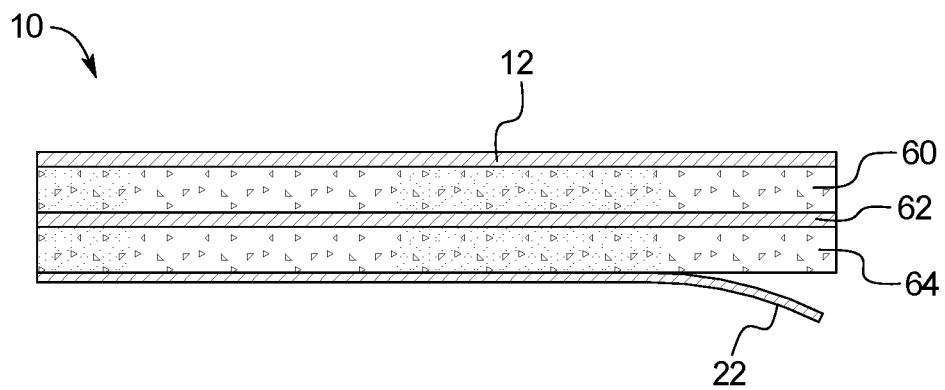
FIG. 6 is a schematic of an example of a delivery system including a multilayer drug adhesive.

FIG. 6 includes a schematic of an example of a multilaminate and/or multi-layer drug in adhesive layer(s). For example, the treatment system 10 can include a top impermeable backing, a first adhesive impregnated with the magnesium composition 60, a separating membrane 62, a second adhesive impregnated with the magnesium composition 64, and a release liner 22.

Figure 7:
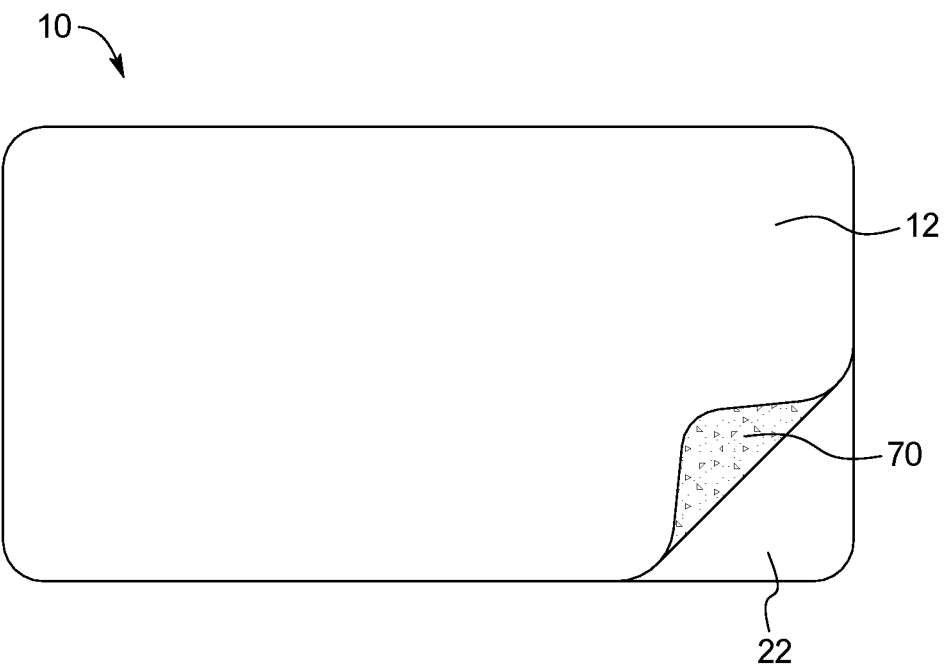
FIG. 7 is a schematic of an example of a delivery system including an impermeable holding material with a porous material for holding a magnesium composition.

FIG. 7 is a top view of an example of a treatment system 10 including a porous material for holding the magnesium composition in a plurality of reservoirs. For example, the treatment system 10 can include a top layer of impermeable backing 12, a porous layer 70 including a plurality of reservoirs 72 for housing the magnesium composition, and a release liner 22.

Figure 8:
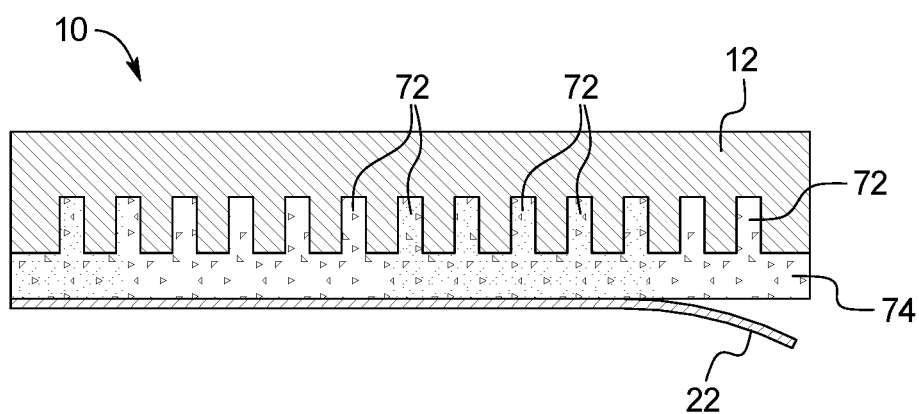
FIG. 8 is a cross-section schematic of an example of a delivery system including an impermeable holding material with a porous material for holding a magnesium composition.

FIG. 8 is a cross sectional view of a treatment system 10 including the porous material for holding the magnesium composition in a plurality of reservoirs. For example, the treatment system 10 can include a top layer of impermeable backing 12, a porous layer 70 including a plurality of reservoirs 72 for housing the magnesium composition, an adhesive layer 74, and a release liner 22.

The dressings are not limited to size, shape or thickness. The dressings can address the need to keep the skin interface at or acceptably near to physiologic pH levels. The pads can be pre-moistened (e.g., at the time of manufacture) with magnesium solutions using any suitable diluent and/or solvent, and any suitable magnesium salt with strengths of the solution to be sufficient to transfer magnesium ions via passive diffusion in sufficient quantity to affect the improvement of plaque psoriasis or other chronic inflammatory conditions. The magnesium solution can be added to an absorbent side of the medical dressing. In an example, 1-10 mL, 1-8 mL, 1-6 mL, 2-4 mL, and/or 1-4 mL of the magnesium solution is added to the dressing.

The composition and dressing could be manufactured in kits that can include the magnesium solution and the dressing wherein the solution is instead provided in a liquid, spray, gel, cream, lotion, or any other suitable composition, wherein the user can apply the composition to the dressing before application. The user can also apply the composition to the skin followed by application of the occlusive or nearly occlusive covering. In an example, the present composition can include the use of other pharmacologic or non-pharmacologic agents that mitigate the sensation of stinging or burning that may be associated with initial use of the invention such as a topical anesthetic or any other agent.

Figure 9:
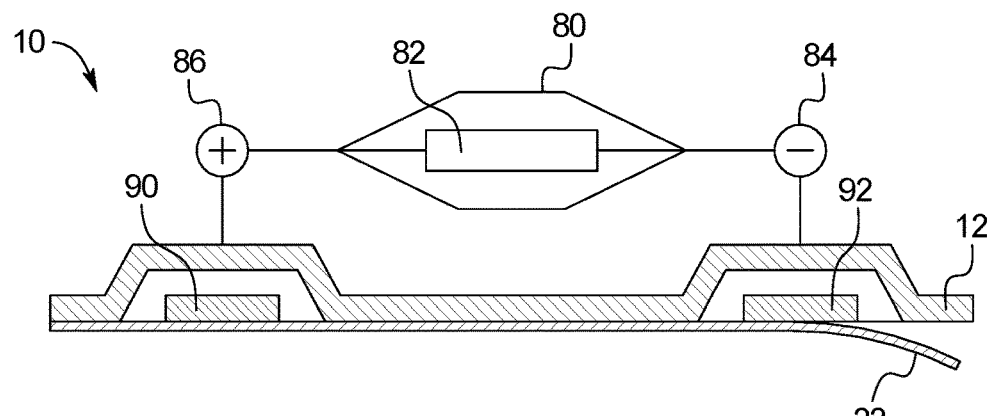
FIG. 9 is a schematic of an example of a delivery system in combination with an iontophoresis.

As shown in FIG. 9, the disclosure also provides the use of pre-loaded iontophoresis patches and kits that enable transdermal delivery of magnesium ions in a sufficient quantity to interrupt the chronic pro-inflammatory mechanism of certain medical conditions. Iontophoresis kits can be packaged with pre-measured amounts magnesium solutions unlimited as to strength or volume or the iontophoresis pad can be pre-loaded with magnesium salt to be placed in solution by the addition of distilled water (or other suitable diluent/solvent) at the time of use. The composition can also be placed in any suitable gel, hydrogel, adhesive, or combination thereof, or any other suitable material capable of holding and dispersing magnesium ions in sufficient quantity to have beneficial therapeutic effect.

In an example, the treatment system can include an impermeable membrane 12 as a top surface, at least two reservoirs, wherein a first reservoir 90 includes the magnesium composition and the second reservoir 92 is inactive, an adhesive, and a release liner. An iontophoresis control device 80 can be used in combination with the iontophoresis patch, wherein the iontophoresis device 80 includes a battery 82, a positive charge source 86, a negative charge source 84, wherein the positive charge source 86 can attach to the first reservoir 90 including the magnesium composition, and the negative charge source 84 can attach to the second reservoir 92.

In an example, the system and method includes applying an iontophoresis pad impregnated with 1-5 mL of a 2-70% wt/vol magnesium complex (magnesium chloride, and/or magnesium sulfate solution in water), and administering a 70-90 mA dose at a positive setting of 1-3 mA for 10-30 minutes. For example, the iontophoresis pad can be impregnated with 1-3 mL of a 2-60% wt/vol, 2-50% wt/vol, 2-10% wt/vol, and/or 2-5% wt/vol of magnesium complex. Such application can be used independently or after the application of a number of doses of medical dressings. For example, after 10-15 applications of medical dressings impregnated with the magnesium solution, the method can further include applying an iontophoresis patch to the psoriasis outbreak and administering a 70-90 mA dose at a positive setting of 1-3 mA for 10-60 minutes.

The present disclosure also includes a treatment method for an inflammatory disorder including providing the magnesium composition on a medical dressing and/or iontophoresis pad to an inflamed or pained portion of the body. In an example, the medical dressing can be impregnated with 1-6 mL of a magnesium composition of a 20-70% wt/vol, 20-50% wt/vol, 20-60% wt/vol, and/or 20-40% wt/vol of a magnesium complex. In an example, the iontophoresis pad can be impregnated with 1-3 mL of a 2-60% wt/vol, 2-50% wt/vol, 2-10% wt/vol, and/or 2-5% wt/vol of magnesium complex. In an example, the iontophoresis patch can include 1-6 mL of a magnesium composition including 5-70% wt/vol of a magnesium complex in water. The method can include delivering 30-50 mA at a setting of 0.5 mA/minute for 1-8 hours. The iontophoresis patch can be replaced with a new patch and the method can include a second treatment of 30-50 mA at a setting of 0.5 mA/minute for 1-8 hours. The replacement method can be performed 2-10 times and/or until the pain subsides.

In an example, the kits can include the magnesium solution and the medical dressings and/or iontophoresis pad wherein the solution is not saturated in the pad, but instead provided in a liquid, cream, spray, gel, hydrogel, or other suitable composition wherein the user can apply the composition to the dressing before application. The disclosure is not limited to specific size, shape, voltage, electrical current, steady or pulsed electrical current, or area size of the electrode patch to be used. The disclosure could also comprise any delivery system not powered by an electrical source similar in nature to a nicotine patch or a lidocaine patch with or without a micropore membrane that can modulate the rate of diffusion.

Figure 10:
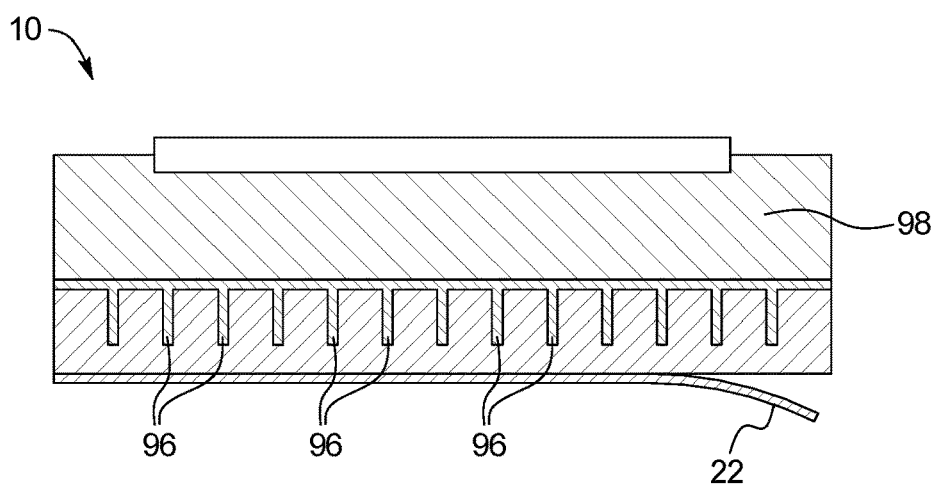
FIG. 10 is a schematic of an example of a delivery system including an optional sealed drug delivery with hollow microneedles.
Figure 11:
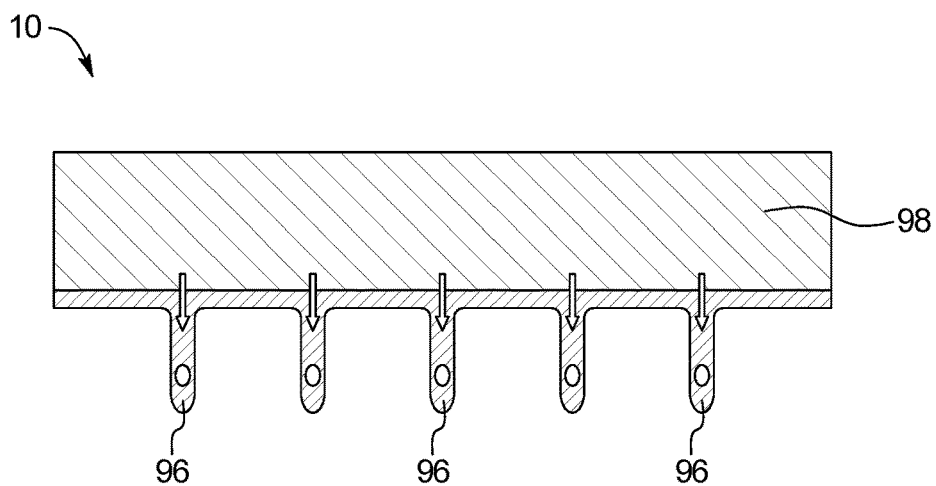
FIG. 11 is a cross-section schematic of an example of a delivery system including an optional sealed drug delivery with hollow microneedles.

In yet another example, the treatment system can include a sealed drug delivery system with hollow microneedles 96 extending from a membrane to penetrate the stratum cornium layer of the skin, as shown in FIGS. 9-10.

In an example, the drug reservoir delivery system can include any suitable impermeable backing material, including, but not limited to, silicone, ethylene vinyl acetate copolymers, polyesters, polyethylene, polycarbonates, polyvinyl chlorides, polyvinylidene, or laminate combinations manufactured to have suitable flexibility.

The drug reservoir delivery system can the use of a plurality of hollow microneedles extending from a separate permeable scaffold or permeable structural membrane, of sufficient length to extend through the adhesive layer or film and create breaks or disruptions in the stratum corneum layer of the skin to positively affect diffusion of magnesium ions through the skin.

The plurality of hollow microneedles can extend from the surface of, and incorporated into, the rate controlling membrane of sufficient length to extend through the layer or film of adhesive to create breaks or disruptions in the stratum corneum layer of the skin to positively affect diffusion of magnesium ions through the skin. The inner diameter of the microneedles can be varied to control rate of flux.

A plurality of microblades can extend from the surface of the rate controlling membrane, or separate permeable polymer scaffold, of sufficient length to extend through the layer or film of adhesive to create breaks or disruptions in the stratum corneum layer of the skin to positively affect diffusion of magnesium ions through the skin.

In an example, 1-10 mL of 50-70% of a magnesium complex (e.g., magnesium chloride, magnesium chloride, or combinations thereof) applied to a medical dressing (e.g., the cotton 4×4 inch gauze, 4×4 in., 3.75×3.75 in.) for an approximate average dose 200-300 mg of magnesium complex per square inch treated for a total of 30-50 hours over five 6-8 hour applications. For example, 1.8 mL of the 58% magnesium solution can be placed on the waterproof pads (i.e., dressing) for an approximate average dose of 160-200 mg per square inch of skin treated for a total of 90-110 hours over 4-10 applications. In an example, over a four week period there can be approximately 150-200 mg of magnesium chloride in solution per square inch of treated skin applied for a total of 130-150 hours in 10-12 divided applications over a four week period which was effective in causing the remission in plaque psoriasis.

There can be passive diffusion of magnesium ions through the inflamed skin of plaque psoriasis that is still relatively small and would not dramatically change the concentration gradient of magnesium ions through the skin over short amounts of time such as 4-8 hours. Taking into account Fick's Law of diffusion where diffusion is directly proportional to time and ion gradient, twelve daily applications of solution containing 200-210 mg of magnesium chloride per square inch of skin treated for twelve hours per day on twelve consecutive days (144 hours total application) should allow for diffusion of a similar quantity of magnesium ions through the skin.

In another example, 24 daily applications of 206 mg of magnesium chloride in solution per square inch of treated skin for 6 hours per day on 24 consecutive days (144 hours total application) should allow for diffusion of a similar quantity of magnesium ions through the skin to have a similar effect. The pads can be applied daily or every other day for periods of 8-12 hours allowing the patient or health care professional to assess the effect on the treated area. The length of treatment can be anticipated to be between 12 days and 36 days. The length of treatment may need to be extended when a slower response is observed in any given individual.

In an example for treatment of plaque psoriasis on an arm, the system can include a 4 in.×4 in., 3 mm thick silicone dressing with an array of 1.5 mm deep and 0.5 mm wide pores acting as a drug reservoir pre-filled with 2 cc of 15% magnesium chloride with an easy release liner applied to the plaque psoriasis and kept in place for 8-24 hours with a 15-20 mm Hg graduated compression sleeve.

In yet another example for treatment of plaque psoriasis on an arm, the system can include a 4 in.×3 in., 3 mm thick silicone dressing with an array of 1.5 mm deep and 0.5 mm wide pores acting as a drug reservoir pre-filled with 3 cc of 15% magnesium chloride coated with a hydrophilic rate limiting adhesive with an easy to remove release liner to be applied to the plaque psoriasis to be worn for 12 to 48 hours.

For example, an embodiment can have a solvent or diluent reservoir with a rate controlling polymer membrane. The solvent or diluent could be contained in a suitable hydrogel of sufficient viscosity to allow release upon removal of the release liner. The solvent or diluent, when released, would dissolve or dilute composition as solution, as saturated solution, or as crystalline form in a polymer matrix reservoir, hydrocolloid reservoir, or any other suitable material for holding the composition in reserve thereby allowing magnesium ions available for diffusion through the skin surface for rate controlled flux.

In an example, the system can have a solvent or diluent reservoir with a rate controlling polymer membrane. The solvent or diluent can be contained in a thin easily breakable plastic, polymer, or other suitable membrane partitioning the solvent/diluent reservoir to be broken prior to application simply by feeling and breaking the containing device thus activating the patch. The solvent, when released, would dissolve or dilute composition as solution, as saturated solution, as crystalline form or any combination thereof, in a suitable hydrocolloid reservoir, or other suitable material capable of holding the composition in reserve, thereby making magnesium ions available for diffusion through material the skin surface.

For example, the system can include a solvent or diluent reservoir with a rate controlling polymer membrane. The solvent, when released, can dissolve or dilute composition in crystalline form coated with varying thicknesses, ranging in thickness of 1 to 220 microns, of dissolvable material such cellulose, polymethacrylates, PEGs or other suitable materials creating dissolvable time release microspheres. The dissolvable microspheres can be dispersed in a polymer matrix, in a hydrocolloid, or any other material found suitable for reservoir, thereby allowing magnesium ions available for controlled diffusion through the skin surface.

The systems and methods can be used for various conditions known to be associated with increased TNF alpha levels including, but not be limited to, psoriasis, plaque psoriasis, bursitis, tendonitis, tennis elbow, planter fasciitis, chronic back or neck pain, anklylosing spondylitis, rheumatoid arthritis, chronic pain syndromes, neuropathic pain, complex regional pain syndrome, chronic wounds, Alzheimer's disease, and/or eczema. The present system and method is also effective in the treatment of another chronic inflammatory disorder associated with increased TNF alpha level, such as adhesive capsulitis and chronic low back pain.

One skilled in the art would have had great reluctance to use a salt solution of this strength applied to diseased skin involved in a pathologic inflammatory response for fear of irritating the diseased skin causing exacerbation of the disease process and harm to the individual to which it is applied. One skilled in the art would also have great reluctance to use a salt solution of this magnitude for fear it would irritate healthy skin in proximity to the diseased skin being treated thus causing spread of the plaque psoriasis disease process via the Koebner phenomenon causing further harm to the individual being treated. Hydrophilic and ionic molecules may be poor candidates for transdermal drug delivery due to the barrier constraints of a lipophilic stratum corneum, the nature being that only smaller lipophilic drugs were considered good drug candidates for transdermal applications.

In contrast, in an example, the present composition includes only one ingredient, magnesium ions, applied in sufficient quantity to interrupt the uncontrolled pro-inflammatory cyclical pathway allowing the disease process to regress allowing normalization of the skin barrier function on its own. The disclosed systems and methods take advantage of the increased permeability of the skin caused by barrier dysfunction in plaque psoriasis, which allows sufficient passive diffusion of magnesium ions to affect the disease process itself. In contrast, the conventional methods see improvement in the barrier function which would inhibit passive diffusion of the skin barrier. The introduction of additional cations and humectants may limit the passive diffusion of the magnesium cations.

It is hypothesized that the mechanism of action is that transdermal absorption of the magnesium cations directly or indirectly down-regulated the production of TNF-alpha thereby breaking the pro-inflammatory feedback mechanism thought to be responsible for the perpetuation of the chronic inflammation in plaque psoriasis. This would be reminiscent of the effect magnesium ions played in the down regulation of TNF-alpha in pre-eclampsia placentas. It should be understood that the disclosure is not limited by the hypothetic mechanism. Regardless of the mechanism of action of topical magnesium, which the disclosure is not limited to, the topical magnesium cations have been shown to have a beneficial effect as a solitary agent in plaque psoriasis when kept in direct contact with the skin for sufficient times and with sufficient strengths.

The present systems and methods can include the use of ions other than magnesium, which may be found to have further beneficial effects when combined with the magnesium ions for treating a particular disease entity or may be found necessary to limit detrimental effects such as bone mineralization, demineralization or remodeling that may be found to be associated with longer term use or any other possible detrimental effect that may be found to occur. For example, the composition can be modified to be useful to effect bone mineralization, demineralization or bone remodeling by introducing yet to be determined ratios of cations such as magnesium, calcium, sodium, potassium and/or others as well as anions such as phosphate, carbonate, chlorine and/or others to be used as a treatment of osteoporosis, osteopenia or other bone related maladies or to affect a more rapid healing of bone fractures.

The systems and methods can include the addition of other pharmacologic agents to the magnesium solution for improving the beneficial effects or limiting detrimental effects related to the use of the invention in any given disease process. The composition can include any pharmacologic agent or permeability enhancing agent that can be used with the device, in the device, in the solution, in the solvent, on the dressing application surface, or on the iontophoresis pad that may increase permeability of the skin to effectively benefit the transdermal transfer of magnesium or other ions through the skin surface. The systems and methods can include the use of micro-needles, solid or hollow, metal or polymer, of any sufficient length to positively affect passive diffusion of magnesium ions through the skin by creating breaks or micro-pores in the stratum corneum layer of the skin. The systems and methods can include the use of microblades of any sufficient length to positively affect the passive diffusion of magnesium ions through the skin by creating breaks or disruption in the stratum corneum layer of the skin.

In addition, the present disclosure provides treatment for chronic inflammatory conditions of chronic lumbar back pain or adhesive capsulitis with an appropriate sized hydrocolloid membrane (e.g., 4 inch×4 inch, 5 inch×5 inch, etc.) and a hydrophilic adhesive at the treatment surface, an impermeable backing layer made of polyester and a florosilicone release liner. The interface surface can be pre-moistened at the surface with 400-600 mg (e.g., 500 mg) magnesium chloride dissolved in 1-3 mL (e.g., 1.2 mL) of water or aqueous solvent (e.g., ethanol, methanol, propylene glycol, etc.) combination to be worn for 8 to 48 hours. In an example, the magnesium composition can be 2-50 wt % in water (e.g., a 35 solution prepared by using 120 mg of $MgCl_2$ in 4 mL of water).

In an example for the treatment of chronic inflammatory conditions, an appropriate sized hydrocolloid membrane with a hydrophilic adhesive at the treatment surface, an impermeable backing layer made of vinyl and a silicone release liner can be used. The interface surface can pre-moistened at the surface with 600-800 mg (e.g., 700 mg) magnesium chloride dissolved 1-5 mL of water or water or aqueous solvent to be worn for 8 to 48 hours. In an example, a 5 inch×5 inch pre-moistened hydrocolloid membrane with a tacking agent pre-moistened with 800 mg magnesium chloride dissolved in 2 mL sterile distilled water or water solvent combination with a polyethylene backing layer and a fluoropolymer release liner to be worn for 1 to 4 days can be used.

In an example for the treatment of adhesive capsulitis, the system includes an electrophoresis patch to be held in place by with circumferential adhesive. The active electrode can be pre-loaded with 150-300 mg (e.g., 200 mg) magnesium sulphate salt in the positive iontophoresis electrode pad 18 sq cm in area to be applied over the affected area after the magnesium salt is placed into solution by adding 4 mL of sterile distilled water or water solvent combination which accompanied the device in a sealed easily opened plastic container. The negative electrode can buffered and relied on self adhesive hydrogel impregnated with sodium chloride with a removable plastic liner. The device can deliver 0.3 mA current at a steady rate over 4 hours for a total delivered dose of 72 mA-min.

In an example, the treatment of adhesive capsulitis can include a self contained iontophoresis device containing a reservoir of 80 mg of magnesium chloride dissolved in 4 mL of sterile water contained and sealed in the positive electrode compartment. The surface of the active electrode contains a membrane embedded with an array of hollow micro-needles 1.0 millimeter in length with the inner diameter of the hollow needles acting in a rate limiting manner to deliver the magnesium ions over 60 minutes with a delivery rate of 1 mA per minute over sixty minutes for a dose of 60 mA-min.

Vast numbers of people with magnesium deficiency rely on various oral supplements to increase serum and/or intracellular magnesium levels for relief of symptoms related to magnesium deficiency. Oral supplementation has inherent problems such as poor and inconsistent absorption in the gastrointestinal tract, the common side effect of diarrhea which further limits the consistency of absorption per given dose, and a myriad of magnesium preparations used as supplements which all have differing bioavailability characteristics. The benefit of magnesium supplementation via iontophoresis or transdermal delivery is that specific and controlled amounts of magnesium ions can be delivered into the body. Therefore, the present systems and methods are suitable for treating magnesium deficiency and the symptoms associated with magnesium deficiency. These would include but not be limited to migraine headaches, cluster headaches, anxiety, fibromyalgia, leg cramps, muscle cramps, certain cardiac arrhythmias, hypertension, and asthma.

It should be noted that various changes and modifications to the embodiments described herein will be apparent to those skilled in the art. Such changes and modifications may be made without departing from the spirit and scope of the present invention and without diminishing its attendant advantages. For example, various embodiments of the systems and methods may be provided based on various combinations of the features and functions from the subject matter provided herein.

Example 1

In an example, two 12 ply cotton gauze sponges (Moore-Brand 4"×4" item #12279) were moistened with 6 cc of the 58% wt/vol magnesium chloride solution. The moistened pad was placed flat in direct contact with an oval psoriasis plaque measuring approximately 2½ inches×4 inches on the lateral aspect of my right knee. The moistened 4×4 was kept in place by wrapping the knee and the positioned pad in a circumferential manner two times using 12 inch wide plastic wrap (similar to Saran wrap) as an occlusive covering. The pad in contact with the psoriasis plaque and held in place by the plastic wrap was then circumferentially secured proximally and distally with 3M Medipore 1 inch wide soft cloth surgical tape. This application was put in place at bed time and kept place for 8 hours while sleeping. This method of application was applied every other day for five applications. The moistened gauze migrated under the plastic wrap off of the psoriatic plaque during sleep. The psoriasis plaque, however, remained damp to touch due to the occlusive nature of the dressing despite the migration.

Example 2

To remedy the migration of the moistened gauze the next seven applications were altered. Johnson+Johnson Large Sterile Waterproof Pads with QUILTVENT™ Technology were obtained. These are similar to large waterproof bandaids measuring 2.875 inches×4 inches with a central pad that measured 1.85 inches×3 inches. Prior to applying the large waterproof pads, the central pad area was moistened with 1.8 cc of the 58% wt/vol magnesium chloride solution and placed centrally on the remaining area of the psoriasis plaque. These applications were applied every third night and kept in place for 8 hours for three applications. The following three applications were also placed every third night and kept in place for 24 hours. The last application was placed again on the following third night and kept in place for eight hours.

The erythema and scales of the plaque started to improve within 24 hours following the first application and continued to improve between applications. By day 14 there was dramatic clinical remodeling of the skin with approximate 85% to 90% clinical improvement. When the solution was kept in place for the 24 hour periods small 2-4 mm painless flat scabs developed over what was previously the psoriasis plaque. These were thought be part of the skin remodeling process and resolved with days. By the start of week four complete remission was obtained with only mild residual hyper-pigmentation related to the chronic inflammation of plaque psoriasis over many years. After placement of the twelfth pad the use of pads were discontinued.

Further, prophylactic spraying of approximately 1 mL of a 50% wt/vol magnesium chloride solution to the area where the psoriatic patch had previously been continued once daily every morning after showering. This solution was made by dissolving the magnesium flakes with distilled water (Hinkley Springs). Applications were continued once daily with application approximately 1 cc of the 50% wt/vol magnesium chloride spray as a prophylactic measure continues into the fourth month after which these applications were discontinued.

The rapidity of the resolution of inflammation, restructuring of the skin and complete remission in as little as four weeks was unexpected.

Complete remission of the psoriatic lesion continued into the twelfth month at which time a one cm recurrent psoriatic patch with associated inflammation and scaling started to redevelop. Occlusive treatment with tapes and hydrocolloid dressings have long been known to have beneficial effect on plaque psoriasis without the use of medication. In an effort to determine whether magnesium ions are inherently beneficial in treating plaque psoriasis without benefit of the occlusive dressing, the recurrent plaque psoriasis was treated with intra-dermal injections of 1 cc of 1% $MgSO_4$ solution once daily for four consecutive days. The injected area was not covered. The $MgSO_4$ solution was made by diluting 0.2 cc of 50% $MgSO_4$ (Fresenius Kabi, LLC, Lake Zurich, Ill. NDIC 63323-064-10) with sterile water, (Hospsira NDC 0409-4887-17) to make 10 cc of 1% $MgSO_4$ solution) once daily for 4 days. The injections directly into the skin were performed to illustrate an inherent benefit from the magnesium ions without the use of occlusion. There was reduction in the inflammatory process and erythema over the next few days with 80% resolution of scaliness and erythema at day 14 following the injections.

On day 16, 1.5 cc of 50% Fresenius Kabi, LLC, Lake Zurich, Ill. NDIC 63323-064-10) was placed on a small iontophoresis pad (Buffered Iontophoresis Electrode Kit Pro Advantage by NDC, INC. La Vergne, Tn.). The iontophoresis dose was delivered over the affected area with a Dynatron Ibox (Dinatronics Corporation, Salt Lake City, Utah) with a 40 mA dose delivered with a positive setting of 2.0 mA over twenty minutes.

On day 18, a second 1.5 cc of 50% $MgSO_4$ was applied to the same type of iontophoresis electrode and delivered to the affected area with the Dynatron Ibox with an 80 mA dose delivered with a positive setting of 1 mA delivered over eighty minutes. There was further improvement by day 28 the recurrent 1 cm plague psoriasis was thought to have been placed into complete remission with no evidence of inflammation, no scaling and no elevation of the previous plaque. Only mild hyper-pigmentation remained which was thought to be related to intra-dermal bleeding from the daily injections four weeks earlier. Once monthly prophylactic treatments were started with 0.8 mL of 50% magnesium chloride solution sprayed onto the surface of 4"×4"DuoDERM™ hydrocolloid dressings and worn for 8 hours periods in an effort to maintain homeostasis between pro-inflammatory and anti-inflammatory mechanisms.

Example 3

In another example, a 61 year old man with plaque psoriasis on the extensor surface of his right knee for over 15 years was started on magnesium treatment. Prior treatment with topical hydrocortisone was stopped two weeks prior. Applications using Johnson+Johnson Large Sterile Waterproof Pads with QUILTVENT™ Technology. 1.8 cc solution of 20% magnesium sulfate solution (APP Fresenius Kabi Lake Zurich, Ill. NDC63323-064-10, 50% solution diluted with sterile water) was applied every third day for eight hour durations. Following 7 applications, the patient noted almost total relief of itching and a 50% reduction in scaling. After the 10 applications of the 20% magnesium sulfate solution, the strength of the solution was increased to 40% for the next ten applications and to 50% for the following 10 applications. Despite increasing the dose of magnesium sulphate there was persistent scaling between applications as well as persistence of dermal hypertrophy of approximately 3 mm thickness having the appearance and feel of a callous. The improvement appeared to have plateaued following the first 10-12 applications.

A trial using a 50% solution of magnesium chloride was made by dissolving the magnesium flakes with distilled water (Hinkley Springs) and applied to the Johnson+Johnson Large Sterile Waterproof Pads with QUILTVENT™. Applications were initially for eight hours every third day. Within days of starting the application of the 50% magnesium chloride solution the patient noted immediate improvement with the further reduction of the fine scaliness and inflammation. The appearance of course scales over the area of dermal hypertrophy appeared. The course scales were thought to be associated with dermal remodeling of the hypertrophic skin likened to the removal of layers of an onion. After 15 applications of the 50% magnesium solution there was elimination of the fine scales, a 90-95% improvement in inflammation and improvement in the dermal hypertrophy. It was decided to continue applications of magnesium chloride until resolution of the dermal hypertrophy. Following the twentieth application the applications were increased to twelve hour duration with frequency increased to every other day. Following this regimen for ten applications dermal hypertrophy had resolved, fine scaliness had resolved and the remodeled skin was pink in nature. Applications were stopped to determine if total remission been achieved. Following two weeks the skin appeared normal attaining color similar to the surrounding skin. When examined with a double polarized light head set apparatus (Syris V600 Vision Enhancement Technology) small erythematous islands were visualized and thought to be residual areas of inflammation not visualized without the apparatus. Treatment was continued for three additional treatments.

Example 4

The present system and method is also effective in the treatment of another chronic inflammatory disorder associated with increased TNF alpha level, such as adhesive capsulitis. The same Johnson+Johnson waterproof pad was applied to normal skin over my right shoulder affected with an exacerbation of adhesive capsulitis. 1.8 cc of the 58% wt/vol magnesium chloride was positioned on the shoulder with no improvement in the pain associated with the adhesive capsulitis after being kept in place continuously for 24 hours. While passive diffusion appears sufficient given the pathologic barrier problems associated with plaque psoriasis, it did not appear sufficient to penetrate normal skin barrier to effect a change in the inflammatory response associated with adhesive capsulitis.

Example 5

A second attempt using transdermal magnesium treatment to affect the pain and inflammation associated with adhesive capsulitis was performed. A 1.3 cc of 50% magnesium sulfate solution (APP Fresenius Kabi Lake Zurich, Ill. NDC63323-064-10) was placed on the positive dispersal pad in an iontophoresis device (iontoPatch 80 manufactured by Travini Medical). The NaCl solution supplied with the device was placed on the negative patch. The positive patch was placed over the tender area on the lateral shoulder and kept in place for 10 hours. It was applied at 8:00 pm and removed the next morning before showering at 6:00 am. There was a notable 40% improvement in the pain associated with active range of motion of the right shoulder after the 10 hours. After showering a second replacement patch prepared in the same manner was placed at 6:15 am, 15 minutes after the first iontoPatch was removed.

The positive side of the patch now placed over a tender area on the anterior shoulder. The second patch application was kept in place for a total of 13.5 hours. After wearing the patches for a total of 12 hours there was an 80% reduction in pain with active range of motion of the affected shoulder. After 16 hours of continued use of the iontoPatch80 with the magnesium sulfate solution there was no pain associated with active range of motion of the affected shoulder. There was no difference between active range of motion of the unaffected left shoulder compared to the active range of motion of the right shoulder which had been affected with adhesive capsulitis causing chronic moderate pain on motion and occasionally severe pain with movement of the shoulder and inability to sleep on the shoulder for the past 4-5 months. The beneficial effect continued in that no further treatment was required over the next 10 months.

The rapid and complete relief of shoulder pain associated with adhesive capsulitis following only 16 hours of transdermal magnesium therapy via iontophoresis was unexpected. It is hypothesized that elevated TNF-alpha levels in certain conditions may be a biomarker for inflammatory related medical conditions that may benefit from the therapeutic effects of localized transdermal magnesium ion treatment.

Example 6

In another example, a trial of transdermal magnesium ions delivered via iontophoresis in an effort to relieve pain, tenderness, and stiffness localized to sacroiliac (SI) joints. A patient with symptoms including exacerbation of chronic low back pain associated with pain, stiffness, and tenderness of both sacroiliac joints with pain radiating to the right iliac crest over a five week period. Symptoms were moderate to severe enough to make standing erect difficult at times and walking was slow and deliberate.

An iontophoresis pad with 120 mg of magnesium chloride diluted in 4 cc of distilled water was placed over the right sacroiliac joint for 80 minutes for delivery of 40 mA minutes with a delivery setting of 0.5 mA/minute at 8:00 pm. Upon waking five hours later and getting out of bed the patient noted a definite improvement of approximately 50% in pain and stiffness of the right SI joint.

A second identical dose was delivered with the same iontophoresis electrodes in place. Following the second treatment of the right SI joint the identical dose with the same iontophoresis settings and same type of electrodes was applied to the left SI joint in which pain and stiffness were unchanged. Ten minutes following delivery of the first dose to the left SI joint a second identical iontophoresis dose was delivered with the same electrodes in place. Two hours following the two treatments on the left SI joint ended there was approximately a 90% reduction in pain and stiffness of the left SI joint. Five hours following the completion of the treatments of the right SI there was an 80% improvement in pain and stiffness. The improvement lasted throughout the next day allowing normal standing and walking with markedly reduced stiffness.

By the third and fourth day pain, stiffness and limitation of movement in the lumbar area recurred despite continued improvement in tenderness over the SI joints. In an effort to determine if passive diffusion of magnesium ions applied over a larger surface area under a hydrocolloid dressing could affect the pain and stiffness of the lower back approximately 0.8 mL of 50% magnesium chloride solution was sprayed on a 4"×4" hydrocolloid patch (DuoDERM™ Extra Thin CGF Dressing, by ConvaTec) and the moist patch was placed over the lumbar spine where the pain was now localized. This was kept in place during an 8 hour period. This resulted in an 80% improvement in pain and stiffness. A second DuoDERM™ patch was prepared in a similar manner and applied to the same area which remained slightly hyperemic from the first application. Application of the second patch was associated with a transient burning sensation. It was thought that the removal of the first hydrocolloid dressing likely caused physical disruption of the stratum corneum and acted as a mechanical permeability enhancer for the application of the second dose similar to tape stripping. The second patch was removed after 90 minutes after resolution of symptoms had occurred. Following use of the magnesium chloride sprayed onto the surface of the DuoDERM™ hydrocolloid dressing for a total of 9.5 hours there was complete relief in the pain and stiffness in the lower back. Complete relief lasted through the next 48 hours. On the third day, there was recurrence of discomfort and stiffness of the lower back. Severity was estimated to be 20% of the original pain and stiffness. A third application of a pre-moistened Duoderm dressing, this time with approximately 0.5 mL of 40% magnesium chloride solution, sprayed onto the surface prior to application to the lumbar spine area and worn for 48 hours continuously. Resolution of discomfort and stiffness occurred after eight hours using the third DuoDERM pre-moistened dressing.

Example 7

In another example, a patient with chronic lower back pain was started on transdermal magnesium therapy. In an effort to determine a threshold for therapeutic response the patient was started on gradually increasing concentrations of magnesium chloride placed on a 4 in.×4 in. hydrocolloid dressing (DupDERM™ Extra Thin CGF, by Convatec). Dosages were always approximately 1 cc sprayed onto surface of the dressing using a 20% solution of Magnesium Chloride (Mylan, NDC 674-134-50) diluted to strengths of 2%, 5%, 10% 15%, and undiluted 20%. Sterile water was used as the diluent (Hospira NDC 0409-4887-17). Dressings were kept in place for 8 hours. This method of application continued with daily graduation in the strength of solution applied. There was no therapeutic improvement in pain or stiffness at dosages of 2% or 5% magnesium chloride solution. Therapeutic benefit was thought to have occurred with a 10% solution with what was estimated to be a 10-20 percent improvement in pain and stiffness after 8 hours. Incremental improvements of pain and stiffness were associated with dosages of 15% and 20%. Pain and stiffness improved by an estimate of the patient by 20-40%. Using the same method of application, the dosages were increased to 30%, 40% and 50% solutions now made with magnesium flakes dissolved in distilled water. These increased dosages were accompanied by incremental therapeutic benefit regarding the improvement in pain and stiffness. The greatest benefit estimated by the patient was over 70% after the 8 hour application of 50% magnesium chloride solution.

For example, an embodiment related to a drug in adhesive delivery system can include any suitable impermeable backing material, such as and without limitation to silicone, ethylene vinyl acetate copolymers, polyesters, polyethylene, polycarbonates, polyvinyl chlorides, polyvinylidene, or laminate combinations manufactured to have suitable flexibility. The application side could have any suitable hydrocolloid adhesive, hydrogel adhesive, or any other suitable adhesive, or combination or laminate thereof, suitable for holding and releasing the magnesium composition to the skin surface for steady and/or controlled flux.

We claim:

1. A treatment method for psoriasis, the method comprising:
   providing a plurality of treatment patches, wherein each treatment patch includes
      a composition including 20-70% wt vol of a magnesium complex in water, and
      a medical dressing, wherein one side of the medical dressing includes 1-6 mL of the composition;
   applying a treatment patch to a psoriasis outbreak for 1 to 24 hours; and
   replacing the applied treatment patch with a new treatment patch every 24-48 hours for 10-40 days.

2. The treatment method of claim 1, wherein the applied treatment patch is replaced every 20-25 hours for 12-36 days.

3. The treatment method of claim 1, wherein the medical dressing includes adhesive for adhering the medical dressing to a patient's body.

4. The treatment method of claim 1, wherein the magnesium complex is magnesium chloride, magnesium sulfate, or combinations thereof.

5. The treatment method of claim 1, wherein the composition includes 1.5-2.5 mL of a 55-60% wt/vol magnesium chloride.

6. The treatment method of claim 1, wherein the composition includes 1.5-2.5 mL of a 20-60% wt/vol magnesium sulfate.

7. The treatment method of claim 1, further comprising
   spraying of a 1 mL solution of a 50% wt/vol of magnesium chloride in water to the psoriasis outbreak.

8. The treatment method of claim 1, further comprising
   applying an iontophoresis pad impregnated with 1-3 mL of a 2-50% magnesium sulfate solution in water; and
   administering a 70-90 mA dose at a positive setting of 1-3 mA for 10-30 minutes.

* * * * *